United States Patent [19]

Aibe et al.

[11] 4,427,630

[45] Jan. 24, 1984

[54] GAS DEODORIZATION METHOD

[75] Inventors: Toshio Aibe, Toyonaka; Yoshio Tsutsumi, Takatsuki; Katsuya Noguchi, Toyonaka, all of Japan

[73] Assignee: Takeda Chemical Industries, Ltd., Osaka, Japan

[21] Appl. No.: 327,736

[22] Filed: Dec. 4, 1981

[30] Foreign Application Priority Data

Dec. 5, 1980 [JP] Japan ................................ 55-172500

[51] Int. Cl.$^3$ ........................ A61L 9/015; A61L 9/00; A61L 9/16
[52] U.S. Cl. ........................................ 422/4; 422/122; 422/171; 422/900; 423/230; 423/237; 423/239; 423/244; 423/245
[58] Field of Search ...................... 422/4, 5, 122, 170, 422/171, 900; 423/230, 237, 239, 244 R, 245

[56] References Cited

U.S. PATENT DOCUMENTS 4,256,728  3/1981  Nishino et al. ......................... 422/4
4,370,301  1/1983  Doi et al. ............................. 422/122

Primary Examiner—Barry S. Richman
Attorney, Agent, or Firm—Wenderoth, Lind & Ponack

[57] ABSTRACT

A sulfur compound and a nitrogen compound as ill-smelling components can efficiently be removed from a gas containing the same by bringing the gas into contact with an adsorbent comprising activated carbon having supported thereon bromine and a non-volatile acid.

10 Claims, No Drawings

GAS DEODORIZATION METHOD

The present invention relates to novel deodorizing adsorbent, which deodorizes efficiently and in one operation an ill-smelling gas containing various kinds of ill-smelling components such as hydrogen sulfide, mercaptans, sulfides, disulfides, ammonia and amines, and to a method of deodorization with the use thereof.

At human waste treatment plants, sewage treatment plants, garbage disposal plants, animal-raising rooms, etc., there is unavoidable evolution of waste gases containing various kinds of ill-smelling components such as sulfur compounds, e.g. hydrogen sulfide, mercaptans, sulfides and disulfides, and nitrogen compounds, e.g. ammonia and amines, and the like which emit bad odors.

Although researches on deodorizing agents or deodorizing methods for individual ill-smelling components have realized their intended results, a mixture of such individually-effective deodorizing agents, when being used for the treatment of gases containing simultaneously a large number of ill-smelling components, does not satisfactorily remove the bad odors.

There have been attempted different processes such as alkali-acid absorption, wet oxidation, ozone oxidation, activated carbon adsorption and combustion processes, but such conventional processes have failed to completely achieve their objectives.

The present inventors, in view of such situation, conducted extensive investigation and, as a result, found that activated carbon having as supported thereon bromine and a non-volatile acid possesses excellent performance in the deodorizing treatment of gases containing as ill-smelling components sulfur compounds such as hydrogen sulfide, mercaptans, sulfides and disulfides and nitrogen compounds such as ammonia and amines.

Thus, the present invention relates to:

1. A deodorizing adsorbent which comprises activated carbon having as supported thereon bromine and a non-volatile acid, and
2. A method of deodorization, which comprises bringing a gas containing a sulfur compound and a nitrogen compound as ill-smelling components into contact with an adsorbent comprising the activated carbon having as supported thereon bromine and a non-volatile acid.

The deodorizing adsorbent of the present invention is obtained by allowing activated carbon to support thereon bromine and a non-volatile acid. The activated carbon as used herein may be of any type which is produced by activating by the known procedures raw materials such as charcoal, coke, coconut shells and resins and exhibits a surface area of 200 to 2000 m²/g. The non-volatile acid as described above includes those whose vapor presure at 50° C. is not higher than 10 mmHg, such as inorganic acids, e.g. sulfuric acid, phosphoric acid and boric acid, and organic acids, e.g. oxalic acid, citric acid and tartaric acid. The amount of the acid to be supported on activated carbon is at a ratio of 1 to 35 wt.%, preferably 3 to 30 wt.%, based on said activated carbon. As the procedure of supporting the acid, by way of example, there may be mentioned a procedure of immersing activated carbon in an aqueous solution of the acid and drying it as occasion demands, and a procedure of spraying activated carbon with an aqueous solution of the acid and drying it if necessary, and the like.

The amount of bromine to be supported on activated carbon is at a ratio of 1 to 30 wt.%, preferably 3 to 20 wt.%, based on the activated carbon. As the procedure of supporting bromine on activated carbon, by way of example, there may be mentioned (I) a procedure of bringing activated carbon into contact with a carrier gas containing bromine gas, (II) a procedure of immersing activated carbon in an aqueous solution containing bromine, followed by drying if necessary, (III) a procedure of spraying activated carbon with an aqueous solution containing bromine or liquid bromine and drying it if necessary, and the like.

In preparing the above mentioned aqueous solution containing bromine, it is convenient and advantageous to dissolve bromine in a 1 to 15 wt.% aqueous solution of a salt as ammonium bromide, sodium bromide, potassium bromide and calcium bromide, because the procedure can permit dissolution of larger amounts of bromine, reduce amounts of water to be used and restrain evaporation of bromine that is strongly toxic.

The order of allowing activated carbon to support thereon bromine and a non-volatile acid is not critical; a non-volatile acid is first supported on activated carbon and then bromine is supported thereon, or bromine is first supported on activated carbon and then a non-volatile acid is supported thereon.

As sulfur compounds which are to be deodorized by the present invention, there may be mentioned, for example, hydrogen sulfide, a mercaptan having 1 to 8 carbon atoms, a sulfide having 2 to 16 carbon atoms and a disulfide having 2 to 16 carbon atoms. As nitrogen compounds which are to be deodorized by the present invention, there may be mentioned, for example, ammonia and an amine having 0 to 18 carbon atoms.

As examples of the mercaptans, there may be mentioned alkyl mercaptans having 1 to 6 carbon atoms such as methyl mercaptan, ethyl mercaptan and propyl mercaptan, and aryl mercaptans having 6 to 8 carbon atoms such as phenyl mercaptan. As the sulfides there may be mentioned, by way of example, alkyl sulfides having 2 to 12 carbon atoms such as methyl sulfide and ethyl sulfide, aryl sulfides having 12 to 16 carbon atoms such as phenyl sulfide, and the like. As examples of the disulfides may be mentioned alkyl disulfides having 2 to 12 carbon atoms such as methyl disulfide and ethyl disulfide and an aryl disulfide having 12 to 16 carbon atoms such as phenyl disulfide and tolyl disulfide. Examples of the amines include alkylamines having 1 to 6 carbon atoms such as methylamine and ethylamine, dialkylamines having 2 to 12 carbon atoms such as dimethylamine, diethylamine and methyl-ethylamine, trialkylamines having 3 to 18 carbon atoms such as trimethylamine, dimethylethylamine and triethylamine, hydrazine, alkylenediamines having 1 to 6 carbon atoms such as methylenediamine, hydroxylamine, hydroxyalkylamines having 1 to 6 carbon atoms such as methanolamine and ethanolamine, acrylamines having 6 to 8 carbon atoms such as aniline, and nitrogen-containing heterocyclic compounds having 1 to 2 rings such as pyridine, pyrrole, indole and skatol.

In the present invention, the gas-solid contacting mode for contacting the ill-smelling gas with the adsorbent is preferably a moving-bed or fixed-bed process, while the space velocity of the gas in each of the adsorbent beds is about 50 to 10,000 hr$^{-1}$, preferably about 360 to 7,200 hr$^{-1}$. The contacting temperature is not higher than about 100° C., preferably 0° to 60° C.

The deodorizing adsorbent according to the present invention exhibits stronger deodorization effect for ill-smelling components than the conventional ones, and its utilization enables deodorization equipment to be made more compact and its running costs to be considerably reduced.

As previously mentioned, the adsorbent comprising the activated carbon having supported thereon bromine and a non-volatile acid, alone, can deodorize in one operation gases containing as ill-smelling components hydrogen sulfide, mercaptans, sulfides, disulfides, ammonia and amines. In deodorizing ill-smelling gases with a particularly high concentration of hydrogen sulfide, however, more efficient deodorization may be possible when such gas is in advance brought into contact with an adsorbent comprising activated carbon which may have as supported thereon iodine and/or an iodine compound, and then treated with the adsorbent comprising the activated carbon having as supported thereon bromine and a non-volatile acid according to the present invention. Adsorbent comprising activated carbon having as supported thereon iodine or an iodine compound is obtained, for example, by allowing iodine or an iodine compound to be supported on activated carbon having a specific surface area of 200 to 2000 $m^2/g$ produced by activating charcoal, coke, coconut shells, etc. by means of conventional procedures. Examples of the iodine compound include iodides of alkali metals such as sodium iodide, potassium iodide, lithium iodide and cesium iodide, and iodides of alkaline earth metals such as calcium iodide, barium iodide, magnesium iodide and strontium iodide, as well as ammonium iodide and the like.

The amount of iodine or an iodine compound to be supported on activated carbon is at a ratio of 0.5 to 15 wt.%, preferably 1 to 10 wt.%, as iodine based on the activated carbon. Normally, it is desirable to use iodine as an aqueous solution in conjunction with potassium iodide or as a solution in an organic solvent (for example, methanol, ethanol, etc.). As the supporting procedure, there may be mentioned, by way of example, a procedure of immersing activated carbon in an aqueous solution of iodine or an iodine compound and drying it, if necessary, a procedure of spraying activated carbon with an aqueous solution of iodine or an iodine compound, followed by drying if necessary, and others.

Contact of the ill-smelling gas with the adsorbent comprising activated carbon or activated carbon having as supported thereon iodine or an iodine compound is conducted in a manner similar to that of the contact of the gas with the adsorbent comprising activated carbon having as supported thereon bromine and a non-volatile acid.

In practicing the present invention, treatment of a gas containing ill-smelling components in advance with the adsorbent comprising activated carbon or activated carbon having as supported thereon iodine or an iodine compound permits efficient treatment of such ill-smelling gas, and also secures extension of the service life of the activated carbon having as supported thereon bromine and a non-volatile acid according to the present invention.

EXAMPLE 1

Activated carbon A: Granular activated carbon of 4 to 6 mesh (BET specific surface area of 1270 $m^2/g$)

Adsorbent B: Activated carbon A having as supported thereon 15 wt.% of phosphoric acid and 10 wt.% of bromine (moisture content of 25%)

Adsorbent C: Activated carbon A having as supported thereon 15 wt.% of phosphoric acid (moisture content of 25%)

Adsorbent D: Activated carbon A having as supported thereon 10 wt.% of bromine (moisture content of 25%)

Adsorbent E: A 1:1 mixture of Adsorbent C and Adsorbent D

Adsorbent F: Activated carbon A having as supported thereon 30 wt.% of phosphoric acid (moisture content of 25%)

Adsorbent G: Activated carbon A having as supported thereon 20 wt.% of bromine (moisture content of 25%)

Adsorbent H: A 1:1 mixture of Adsorbent F and Adsorbent G Adsorbents B through H were packed into the columns I through VI of 4 cm $\phi$ inner diameter in the states as described in Table 1.

Passed through each of these columns at a linear flow rate of 30 cm/sec was air at 25° C. (relative humidity of 80%) containing 0.78 ppm of $CH_3SH$, 0.36 ppm of $(CH_3)_2S$, 0.64 ppm of $(CH_3)_2S_2$, 1.8 ppm of $NH_3$ and 0.21 ppm of $(CH_3)_3N$, whereby the gas flowing out of the outlet of the column was investigated for smell and components by means of gas chromatography. The results are tabulated in Table 1.

TABLE 1

| Column No. | Packed state of adsorbent in the column | | Deodorization effect |
|---|---|---|---|
| I (present invention) | Adsorbent B-30 $cm^L$ | | Remained odorless 120 days later, with highly good deodorization effect. 125 days later, methyl sulfide leaked in slight amount (0.05 ppm) |
| II (control) | (on the side of gas inlet) Adsorbent C-30 $cm^L$ | (on the side of gas outlet) Adsorbent D-30 $cm^L$ | Remained odorless 120 days later, with highly good deodorization effect. 125 days later, methyl sulfide leaked in slight amount (0.05 ppm). |
| III (control) | (on the side of gas inlet) Adsorbent D-30 $cm^L$ | (on the side of gas outlet) Adsorbent C-30 $cm^L$ | 12 days later, $(CH_3)_2S$ (0.05 ppm) began to leak, as its smell was perceived. |
| IV (control) | Adsorbent E-30 $cm^L$ | | 21 days later, $(CH_3)_2S$ (0.05 ppm) began to leak, as its smell was perceived. |
| V (control) | (on the side of gas inlet) Adsorbent F-15 $cm^L$ | (on the side of gas outlet) Adsorbent G-15 $cm^L$ | $(CH_3)_2S$ (0.05 ppm), 58 days later, and ammonia (0.1 ppm), and trimethylamine (0.02 ppm), 69 days later, began to leak, as their smells were perceived |
| VI (control) | Adsorbent H-30 $cm^L$ | | 44 days later, $(CH_3)_2S$ (0.05 ppm) began to leak, as its smell was perceived. |

EXAMPLE 2

Activated carbon I: Granular activated carbon of 4 to 6 mesh (BET specific surface area of 1150 $m^2/g$)

Adsorbent J: Activated carbon I having as supported thereon 15 wt.% of phosphoric acid and 10 wt.% of bromine (moisture content of 25 wt.%)

Adsorbent K: Activated carbon I having as supported thereon 5.0 wt.% of NH$_4$I (moisture content of 25 wt.%)

Activated carbon I and adsorbents J and K were packed, from the side of gas inlet to the side of gas outlet, into PVC(polyvinyl chloride)-made columns of 4 cm inner diameter to 30 cm of their respective layer height in the order as described in Table 2.

Air at 25° C. (relative humidity of 80%) containing 1.2 ppm of H$_2$S, 0.51 ppm of CH$_3$SH, 0.19 ppm of (CH$_3$)$_2$S, 0.13 ppm of (CH$_3$)$_2$S$_2$, 1.2 ppm of NH$_3$ and 0.13 ppm of (CH$_3$)$_3$N was passed through each of these columns at a linear flow rate of 30 cm/sec, whereby the gas flowing out of the outlet of the column was investigated for smell and components by means of gas chromatography. The results are tabulated in Table 2.

TABLE 2

| Column No. | Packing order for each adsorbent and activated carbon | | Deodorization effect |
|---|---|---|---|
| I | (gas inlet layer) I | (gas outlet layer) J | 150 days later, remained odorless, with good deodorization effect. |
| | (present invention) | | |
| II | (gas inlet layer) K | (gas outlet layer) J | 196 days later, remained odorless, with good deodorization effect. |
| | (present invention) | | |
| III | (gas inlet layer) J | (gas outlet layer) I | 21 days later, H$_2$S began to leak as strong smell was perceived. |
| | (control) | | |

EXAMPLE 3

A 2.4 l portion each of Activated carbon A of Example 1 and Adsorbent B of Example 1 were packed into a PVC-made column of 10 cm $\phi$ inner diameter on the sides of a gas inlet and gas outlet, respectively. A ventilated gas from storage tanks in a sewage treatment plant was passed through the column at a linear flow rate of 30 cm/sec at ambient temperature. The gas contained the following components (each in average concentration): 152 ppb of hydrogen sulfide, 95 ppb of methyl mercaptan, 60 ppb of methyl sulfide, 13 ppb of methyl disulfide, 325 ppb of ammonia, 9 ppb of trimethylamine, 25 ppb of benzene, 80 ppb of toluene, 95 ppb of xylene, and about 180 ppb of other aromatic hydrocarbons (inclusive of many components such as high-boiling aliphatic hydrocarbons, e.g. other decanes, etc., aldehydes, lower fatty acids, halogenated hydrocarbons, phenols, and the like).

The gas issuing from the outlet of the column remained odorless even after continuous operation for 180 days, whereby concentrations of hydrogen sulfide, methyl mercaptan, methyl sulfide, methyl disulfide, ammonia and trimethylamine were found to be all not higher than 1 ppb.

In the case of Adsorbent K of Example 2 being utilized in place of Activated carbon A, the gas from the column outlet remained odorless even after continuous operation for 210 days, with strong deodorization effect achieved.

EXAMPLE 4

Activated carbon A of Example 1 was crushed and sieved to particle size of 16 to 24 mesh, and was allowed to have supported thereon each of the acids and bromine, at the ratios, as indicated in Table 3 to prepare adsorbents (each adsorbent showed moisture content of 25 to 30 wt.%).

The samples thus obtained were each packed into a 1.6 cm $\phi$ column to the layer height of 7.5 cm, followed by passing through the column air (25° C. of temperature and 80% of relative humidity) containing 0.5 ppm of (CH$_3$)$_2$S and 1.5 ppm of (CH$_3$)$_3$N at a linear flow rate of 40 cm/sec, to conduct a removal test on methyl sulfide and trimethylamine. The results are shown in Table 3.

EXAMPLE 5

The activated carbon (16 to 24 mesh) having as supported thereon the same acids as in Example 4 and bromine was each packed into a 1.6 cm $\phi$ column to the layer height of 7.5 cm, followed by passing through the column at a linear flow rate of 40 cm/sec air (25° C. of temperature and 80% of relative humidity) containing 3.0 ppm of CH$_3$SH and 1.5 ppm of NH$_3$, to conduct a removal test on methyl mercaptan and ammonia. The results are shown in Table 4.

TABLE 3

| Acid supported and its amount | Amount of bromine | Percent removal of (CH$_3$)$_2$S at the time-points shown below | | | Percent removal of (CH$_3$)$_3$N at the time-points shown below | | |
|---|---|---|---|---|---|---|---|
| | | 50 hrs. later | 100 hrs. later | 150 hrs. later | 50 hrs. later | 100 hrs. later | 150 hrs. later |
| H$_2$SO$_4$-5 wt % | 10 wt % | 100 | 100 | 96 | 100 | 100 | 93 |
| H$_2$SO$_4$-10 wt % | 10 wt % | 100 | 100 | 100 | 100 | 100 | 100 |
| H$_3$PO$_4$-3 wt % | 10 wt % | 100 | 98 | 40 | 100 | 95 | 35 |
| H$_3$PO$_4$-5 wt % | 10 wt % | 100 | 100 | 75 | 100 | 98 | 64 |
| H$_3$PO$_4$-10 wt % | 10 wt % | 100 | 100 | 99 | 100 | 100 | 96 |
| H$_3$PO$_4$-15 wt % | 5 wt % | 100 | 90 | 38 | 100 | 98 | 33 |
| H$_3$PO$_4$-15 wt % | 10 wt % | 100 | 100 | 100 | 100 | 100 | 100 |
| H$_3$PO$_4$-15 wt % | 15 wt % | 100 | 100 | 100 | 100 | 100 | 100 |
| H$_3$PO$_4$-20 wt % | 10 wt % | 100 | 100 | 100 | 100 | 100 | 100 |
| oxalic acid-10 wt % | 10 wt % | 100 | 100 | 91 | 100 | 100 | 92 |
| citric acid-10 wt % | 10 wt % | 100 | 100 | 85 | 100 | 100 | 88 |
| Tartaric acid-10 wt % | 10 wt % | 100 | 100 | 82 | 100 | 100 | 73 |
| Control  H$_3$PO$_4$ alone-15 wt % | | 0 | 0 | 0 | 100 | 100 | 100 |
| Br$_2$ alone-10 wt % | | 95 | 53 | 5 | 100 | 78 | 8 |

TABLE 4

| Acid supported and its amount | Amount of bromine | Percent removal of $CH_3SH$ at the time-points shown below | | | Percent removal of $NH_3$ at time points shown below | | |
|---|---|---|---|---|---|---|---|
| | | 50 hrs. later | 100 hrs. later | 150 hrs. later | 50 hrs. later | 100 hrs. later | 150 hrs. later |
| $H_2SO_4$-5 wt % | 10 wt % | 100 | 100 | 99 | 100 | 100 | 95 |
| $H_2SO_4$-10 wt % | 10 wt % | 100 | 100 | 100 | 100 | 100 | 100 |
| $H_3PO_4$-5 wt % | 10 wt % | 100 | 100 | 98 | 100 | 100 | 98 |
| $H_3PO_4$-10 wt % | 10 wt % | 100 | 100 | 90 | 100 | 100 | 96 |
| $H_3PO_4$-15 wt % | 5 wt % | 100 | 98 | 82 | 100 | 100 | 90 |
| $H_3PO_4$-15 wt % | 10 wt % | 100 | 100 | 100 | 100 | 100 | 100 |
| $H_3PO_4$-20 wt % | 10 wt % | 100 | 100 | 100 | 100 | 100 | 100 |
| $H_3PO_4$ alone-15 wt % | | 38 | 0 | 0 | 100 | 100 | 100 |
| $Br_2$ alone-10 wt % | | 70 | 8 | 0 | 81 | 10 | 0 |

EXAMPLE 6

Activated carbon A of Example 1 was crushed and sieved to particle size of 16 to 24 mesh. One part of this carbon was allowed to have supported thereon 15 wt.% of phosphoric acid and 10 wt.% of bromine; another part of the carbon was allowed to have supported thereon 15 wt.% of phosphoric acid only; and the remaining part of the carbon was allowed to have supported thereon 10 wt.% of bromine. These samples showed moisture content of 25 wt.%.

The samples thus obtained were each packed into a 1.6 cm $\phi$ column to the layer height of 7.5 cm, followed by passing through column the air (25° C. of temperature and 80% of relative humidity) containing 0.5 ppm of $(CH_3)_2S$, 0.5 ppm of $CH_3NH_2$ and 1.0 ppm of $(CH_3)_2NH$ at a linear flow rate of 40 cm/sec, to conduct a removal test on methyl sulfide, monomethylamine and dimethylamine. The results are shown in Table 5.

TABLE 5

| Amount of $H_3PO_4$ (wt %) | Amount of $Br_2$ (wt %) | Percent removal of $(CH_3)_2S$ at the time-points shown below | | | Percent removal of $CH_3NH_2$ at the time-points shown below | | | Percent removal of $(CH_3)_3N$ at the time-points shown below | | |
|---|---|---|---|---|---|---|---|---|---|---|
| | | 50 hrs. later | 100 hrs. later | 150 hrs. later | 50 hrs. later | 100 hrs. later | 150 hrs. later | 50 hrs. later | 100 hrs. later | 150 hrs. later |
| 15 | 10 | 100 | 100 | 100 | 100 | 100 | 100 | 100 | 100 | 98 |
| 15 | 0 | 0 | 0 | 0 | 100 | 100 | 99 | 100 | 100 | 96 |
| 0 | 10 | 93 | 45 | 12 | 100 | 83 | 39 | 100 | 79 | 16 |

What is claimed is:

1. A method of deodorization, which comprises contacting a gas containing a sulfur compound and a nitrogen compound as ill-smelling components with an adsorbent consisting of activated carbon having supported thereon bromine and an acid having a vapor pressure at 50° C. of not higher than 10 mmHg, the amount of bromine supported on the activated carbon being 3 to 20 weight % based on the activated carbon.

2. A method as claimed in claim 1, wherein the sulfur compound is hydrogen sulfide, a mercaptan having 1 to 8 carbon atoms, a sulfide having 2 to 16 carbon atoms or a disulfide having 2 to 16 carbon atoms, and the nitrogen compound is ammonia, hydroxylamine, hydrazine or an amine having 1 to 18 carbon atoms.

3. A method as claimed in claim 1, wherein the sulfur compound is hydrogen sulfide, an alkyl mercaptan having 1 to 6 carbon atoms, an alkyl sulfide having 2 to 12 carbon atoms or an alkyl disulfide having 2 to 12 carbon atoms, and the nitrogen compound is ammonia, an alkylamine having 1 to 6 carbon atoms, a dialkylamine having 2 to 12 carbon atoms or a trialkylamine having 3 to 18 carbon atoms.

4. A method as claimed in claim 1, wherein the gas containing a sulfur compound and a nitrogen compound as ill-smelling components is brought into contact with an adsorbent comprising activated carbon before contacting the gas with the adsorbent consisting of activated carbon having supported thereon bromine and the acid.

5. A method as claimed in claim 1, wherein the acid is sulfuric acid, phosphoric acid, boric acid, oxalic acid, citric acid or tartaric acid.

6. A method as claimed in claim 1, wherein the acid is supported on the activated carbon in an amount of 1 to 35 weight % based on the activated carbon.

7. A method as claimed in claim 1, wherein the acid is supported on the activated carbon in an amount of 3 to 30 weight % based on the activated carbon.

8. A method as claimed in claim 1, wherein the gas containing a sulfur compound and a nitrogen compound as ill-smelling components is brought into contact with an adsorbent comprising activated carbon having supported thereon iodine and/or an iodine compound before contacting the gas with the adsorbent consisting of activated carbon having supported thereon bromine and the acid.

9. A method as claimed in claim 8, wherein the iodine and/or iodine compound is supported on activated carbon in an amount of 0.5 to 15 weight % as iodine based on the activated carbon.

10. A method as claimed in claim 9, wherein the iodine compound is an alkali metal iodide, an alkaline earth metal iodide or ammonium iodide.

* * * * *